(12) United States Patent
Nakatsuji et al.

(10) Patent No.: US 7,083,977 B2
(45) Date of Patent: Aug. 1, 2006

(54) MONKEY-ORIGIN EMBRYONIC STEM CELLS

(75) Inventors: Norio Nakatsuji, Kyoto (JP); Takashi Tada, Kyoto (JP); Ryuzo Torii, Moriyama (JP); Yoshihiko Hosoi, Sakai (JP); Akira Iritani, Kyoto (JP); Teruo Akuta, Kumamoto (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 384 days.

(21) Appl. No.: 10/311,146

(22) PCT Filed: Jun. 15, 2001

(86) PCT No.: PCT/JP01/05154

§ 371 (c)(1),
(2), (4) Date: Dec. 13, 2002

(87) PCT Pub. No.: WO01/96533

PCT Pub. Date: Dec. 20, 2001

(65) Prior Publication Data

US 2003/0157710 A1 Aug. 21, 2003

(30) Foreign Application Priority Data

Jun. 15, 2000 (JP) ............................. 2000-180376
Sep. 13, 2000 (JP) ............................. 2000-278057

(51) Int. Cl.
*C12Q 1/68* (2006.01)
*C12N 5/00* (2006.01)
*C12N 5/06* (2006.01)

(52) U.S. Cl. ............................. 435/325; 435/363; 435/6

(58) Field of Classification Search ..................... 435/6
See application file for complete search history.

(56) References Cited

U.S. PATENT DOCUMENTS 5,843,780 A * 12/1998 Thomson ..................... 435/363

FOREIGN PATENT DOCUMENTS

WO    WO 96/22362 A1    7/1996

OTHER PUBLICATIONS

Thompson JA, Pluripotent cell lines derived from common marmoset (*Callithrix jacchus*) blastocysts, 1996, Biology of Reproduction, vol. 55, pp. 254-259.*
Hewitson L, Fertilization and embryo development to bastocyts after intracytoplasmic sperm injection in the rhesus monkey, 1998, Human Reproduction, vol. 13, pp. 3449-3455.*
Sankai T, Cyryopreservation of spermatozoa from cynomolgus monkeys, 1994, J. of Reproduction and Fertility, vol. 101, pp. 273-278.*
Hewitson L, Fertilization and embryo development to blastocyts after intracytoplasmic sperm injection in the rhesus monkey, 1998, Human Reproduction, vol. 13, pp. 3449-3455.*
Thompson JA, Pluripotent cell lines derived from common marmoset (*Callithrix jacchus*) blastocysts, 1996, Biology of Reproduction, vol. 55, pp. 254-259.*
Thomson, James A., et al. Proceedings of the National Academy of Sciences of the USA, vol. 92, No. 17, pp. 7844-7848, Aug. 15, 1995.
Thomson, James A., et al. Current Topics in Developmental Biology, vol. 38, pp. 133-165, 1998.
Thomson, James A., et al. Common Marmoset (*Callithrix jacchus*) Blasocysts, Biology of Reproduction, vol. 55, No. 2, pp. 254-259, Aug. 1996.
Torii, Ryuzo, et al. Primates, vol. 41, No. 1, pp. 39-47, Jan. 2000.
Hewitson, L., et al. Human Reproduction, vol. 13, No. 12, pp. 3449-3455, Dec. 1998.
Miyoshi, Kazuyoshi, et al. Nippon Jusei Chakushou Gakkai Zasshi, Vo. 15, No. 1, pp. 180-182, Feb. 28, 1998.
Torii, R., et al. Theriogenology, vol. 55, No. 1, p. 374, Jan. 1, 2001.
Suemori Hirofumi et al., Developmental Dynamics, vol. 222, No. 2, Oct. 2001, pp. 273-279.

* cited by examiner

*Primary Examiner*—Ram R. Shukla
*Assistant Examiner*—David A. Montanari
(74) *Attorney, Agent, or Firm*—Birch, Stewart, Kolasch & Birch, LLP (57) ABSTRACT

A method for producing a monkey-derived embryonic stem cell comprising the steps of carrying out fertilization by insemination by in vitro fertilization or intracytoplasmic sperm injection using a monkey ovum and monkey sperms, thereby giving a fertilized ovum, allowing the fertilized ovum to differentiate into a blastocyst by in vitro culture, and establishing an ES cell line using the blastocyst; the monkey ES cell obtained by the method, a method for screening a reagent for specific differentiation into cell or tissue by using the ES cell; and a differentiated cell or differentiated tissue each differentiated from the ES cell. According to the present invention, applications of the embryonic stem cells to embryological studies clinical applications, experimental models, and the like on primates, studies of diseases, are expected.

5 Claims, 3 Drawing Sheets

MONKEY-ORIGIN EMBRYONIC STEM CELLS

This application is the national phase under 35 U.S.C. § 371 of PCT International Application No. PCT/JP01/05154 which has an International filing date of Jun. 15, 2001, which designated the United States of America.

TECHNICAL FIELD

The present invention relates to a monkey-derived embryonic stem cell which is useful for embryological studies, studies of diseases, clinical applications, experimental models, and the like on primates, particularly on human and a monkey; a method for producing a monkey-derived embryonic stem cell, by which the monkey-derived embryonic stem cell can be obtained in a high yield; a method for screening a reagent for specific differentiation into a tissue or a cell, which is useful for obtaining the desired differentiated cell or the desired differentiated tissue; and a differentiated cell or differentiated tissue.

BACKGROUND ART

An embryonic stem cell (hereinafter also referred to as ES cell) is an undifferentiated cell having the pluripotency and the ability of self-replication. In addition, it is suggested that the ES cell has the ability to repair damaged tissues. Therefore, intensive studies on ES cells have been conducted, since the ES cells are useful in the screening of therapeutic substances for various diseases, the field of regenerative medicine, and the like.

Currently, mouse-derived ES cells have been widely used in, for instance, the production of an engineered mouse in which a specific gene has been altered by gene targeting, and the like. However, in the case of the application of mouse-derived ES cells on the models of human diseases, the expected effects may not always be obtained for the following reasons: a) there are some genes expressed at different stages between mouse embryos and human embryos; b) the structures or functions of the extraembryonic tissues such as the placentas are different; c) the structures of the embryonic tissues of the early-embryos nidated are different.

On the other hand, monkey-derived embryonic stem cells are suitable for use for the studies of human diseases, because they are more closely related to human, as compared to mouse-derived ES cells.

Although approximately 200 kinds of monkeys have been conventionally known around the world, the types of monkeys used for the routine experiments are limited in the current situations. Higher primates can be roughly divided into the following two groups:

(1) New World Primates

The common marmoset (*Callithrix jacchus*) has been widely known, and used as an experimental primate. The development of the New World primate is basically similar to that of the Old World primate, with some differences regarding the structures of the embryos or the placentas.

(2) Old World Primates

The Old World primate is a primate extremely closely related to human. The rhesus monkey (*Macaca mulatta*) and the cynomolgus monkey (*Macaca fascicularis*) are known. The Japanese monkey (*Macaca fuscata*) belongs to the same genus (the genus *Macaca*) as *Macaca fascicularis*. The development of the Old World primate is extremely similar to that of human.

Currently, as monkey-derived ES cells, the common marmoset ES cells [Thomson, J. A. et al., *Biol. Reprod.* 55, 254–259 (1996)], and the rhesus ES cells [Thomson, J. A. et al., *Proc. Natl. Acad. Sci. U.S.A.* 92, 7844–7848 (1995)] have been established. However, as described above, *Callithrix jacchus* belongs to the New World primates which are not genealogically derived from humans, with some differences in the structures of the embryos or the placentas. Further, since *Callithrix jacchus* is small, the manipulations in various experiments are not easy in the current situations, and there are little background data. On the other hand, *Macaca mulatto* is rarely used as an experimental animal in Japan and Europe. In addition, the reproduction is seasonal, so that the regular ovulation does not necessarily occur throughout the year. Furthermore, there are defects in preparation of the common marmoset ES cells and the rhesus ES cells that the collection of ova is time-consuming and inefficient.

Although human ES cells also have been developed, the use thereof may be limited from the ethical viewpoint.

DISCLOSURE OF INVENTION

The present invention has been accomplished in light of the prior art described above. An object of the present invention is to provide a monkey-derived embryonic stem cell which is useful for embryological studies, studies of diseases, clinical applications, experimental models, and the like on primates, particularly on human and a monkey; a method for producing the monkey-derived embryonic stem cell, by which the monkey-derived embryonic stem cell can be obtained in a high yield; a method for screening a reagent for specific differentiation into a cell or tissue, which is useful for obtaining the desired differentiated cell or the desired differentiated tissue; and a differentiated cell or differentiated tissue.

The gist of the present invention relates to

[1] a monkey-derived embryonic stem cell obtainable by carrying out a process comprising:
 (a) carrying out fertilization by in vitro fertilization or intracytoplasmic sperm injection using a monkey ovum and a monkey sperm, thereby giving a fertilized ovum;
 (b) allowing the fertilized ovum obtained in step (a) to differentiate into a blastocyst by in vitro culture; and
 (c) establishing an embryonic stem cell line using the blastocyst obtained in step (b);

[2] a method for producing a monkey-derived embryonic stem cell, comprising:
 (a) carrying out fertilization by in vitro fertilization or intracytoplasmic sperm injection using a monkey ovum and a monkey sperm, thereby giving a fertilized ovum;
 (b) allowing the fertilized ovum obtained in step (a) to differentiate into a blastocyst by in vitro culture; and
 (c) establishing an embryonic stem cell line using the blastocyst obtained in step (b);

[3] an established cynomolgus monkey-derived cell having the following properties:
 (i) being capable of indefinite proliferation while maintaining an undifferentiated state;
 (ii) having the same chromosome number as that of original *Macaca fascicularis*;
 (iii) exhibiting the pluripotency when transplanted to hypodermis, the renal capsule or the testis of a 8–12 week-old SCID mouse or nude mouse;
 (iv) being negative for SSEA-1 and positive for SSEA-3 and SSEA-4; and
 (v) exhibiting an alkaline phosphatase activity;

[4] a method for screening a reagent for specific differentiation into a tissue or a cell, characterized by maintaining a cell selected from the group consisting of the monkey-derived embryonic stem cell according to item [1] above and the cynomolgus monkey-derived cells according to item [3] above, in the presence of a test substance; and

[5] a differentiated cell or differentiated tissue, resulting from differentiation of an embryonic stem cell selected from the group consisting of the embryonic stem cell according to item [1] above and the cynomolgus monkey-derived cell according to item [3] above.

BRIEF DESCRIPTION OF THE DRAWINGS

FIG. 3 is a photograph showing the results of microscopic observations of the tumors after various stainings, wherein the tumors were formed by injecting subcutaneously the cynomolgus monkey-derived embryonic stem cells of the present invention into a mouse. Panels A to H show the results of microscopic observations of the tumors after HE staining, wherein the tumors were formed by injecting subcutaneously the cynomolgus monkey-derived embryonic stem cells of the present invention into a mouse. Panel A: whole tumor (Bar=300 µm), Panel B: neuroepithelium (Bar=200 µm), Panel C: glia (Bar=200 µm), Panel D: gland (Bar=200 µm), Panel E: muscle (Bar=200 µm), Panel F: cartilage (Bar=400 µm), Panel G: bone (Bar=200 µm), and Panel H: ciliated epithelium (Bar=150 µm). Panels I to M show the results of microscopic observations of the above-mentioned tumors after immunostaining. Panel I: immunostaining of neuron and glia for NSE (Bar=200 µm), Panel J: immunostaining of glia for GFAP (Bar=200 µm), Panel K: immunostaining of peripheral nerve for NSE (Bar=200 µm), Panel L: immunostaining of muscle for desmin (Bar=200 µm), and Panel M: immunostaining of cartilage for S-100 proteins (Bar=400 µm).

BEST MODE FOR CARRYING OUT THE INVENTION

The "monkey" used in the present invention refers to primates, specifically the New World primates and the Old World primates. Among them, the Old World primates are expected to be used as model animals of diseases close to human, or used in a system for screening therapeutic agents for various diseases, because they are primates which are extremely closely related to human, and developmentally resemble human. Therefore, in the present invention, the Old World primates, specifically including *Macaca fuscata* and *Macaca fascicularis*, are desirable, and *Macaca fascicularis* is especially preferable.

The above-mentioned *Macaca fuscata* and *Macaca fascicularis* have closer genealogical relations to humans. Since *Macaca fuscata* is middle-sized (weight: 5 to 15 kg), there are advantages in that a surgical operation can be easily performed on *Macaca fuscata*, and that *Macaca fuscata* has sufficient physical strength. Further, *Macaca fuscata* has docile nature and training of *Macaca fuscata* is greatly successful. Therefore, it is advantageous in that various experiments can be carried out under no anesthesia. On the other hand, since *Macaca fascicularis* is small (weight: 3 to 6 kg), the *Macaca fascicularis* has advantages such that the handling thereof in various animal experiments is easy, and that there are many examples of the use of the *Macaca fascicularis* as a laboratory animal in Japan and Europe, and many background data are obtained. In addition, ovulation occurs throughout the year in *Macaca fascicularis*, so that it is more advantageous in genealogical and physiological experiments than *Macaca mulatta* with seasonal ovulation.

The monkey-derived embryonic stem cell of the present invention can be prepared by a process (hereinafter referred to as a method for producing a monkey-derived embryonic stem cell) comprising:

(a) carrying out fertilization by in vitro fertilization or intracytoplasmic sperm injection using a monkey ovum and a monkey sperm, thereby giving a fertilized ovum;

(b) allowing the fertilized ovum obtained in the step (a) to differentiate into a blastocyst by in vitro culture; and (c) establishing an embryonic stem cell line using the blastocyst obtained in the step (b).

The method for producing a monkey-derived embryonic stem cell is encompassed by the present invention.

The method for producing a monkey-derived embryonic stem cell of the present invention is based on the findings of the present inventors that a blastocyst can be obtained from a fertilized ovum in a surprisingly high probability of about 40 to 46%, since the steps (a) to (c) described above are carried out. Thus, according to the method of the present invention, there can be also exhibited an excellent effect that a monkey-derived blastocyst can be developed in an excellent efficiency. Therefore, according to the method of the present invention, there is exhibited an excellent effect that a monkey-derived embryonic stem cell can be obtained in an extremely high yield, as compared to conventional methods (e.g., WO 96/22362 and the like).

In the step (a), monkey ova can be collected by a method of performing abdominal dissection and ovariocentesis under direct vision, a method of extracting a uterine tube and then washing it, to collect ovulated ova, or other methods. It is desired that ova are collected from a monkey under laparoscopic observation, from the viewpoints of reducing the burden on the animal, shortening or eliminating the time required for wound healing after the surgical treatment and reducing the risk for infection in the animal. Ovum collection under laparoscopic observation may be carried out, for instance, by making an incision of only about 1 cm, inserting a laparoscope, and performing ovariocentesis through the incision in the abdominal wall. Since magnified views of the local site are easily obtained by this process, it is advantageous in that the centesis site can be targeted more accurately to collect ova, as compared to the case where ovariocentesis is performed under direct vision. In addition, collection of an ovum under laparoscopic observation is desirable from the viewpoint of animal welfare, because only one stitch is required to suture the abdominal wall after the ovum collection and the operation can be completed in a short time.

The age of the female monkey used for ovum collection may vary depending on the kind of the monkey. It is desired that the age of the female monkey is 3.5 years old or more, preferably 4 years old or more, from the viewpoint that it is desired to show regular menstrual cycle. In addition, it is desired that the age of the females are 20 years old or less, preferably 15 years old or less, from the viewpoint that they are before the menopause. Specifically, it is desired that *Macaca fuscata* is 5 to 15 year-old and *Macaca fascicularis* is 4 to 15 year-old.

For ovum collection, an ovulation-inducing agent may be used. The ovulation-inducing agent includes follicle-stimulating hormone (FSH), luteinizing hormone (LH), gonadotropin releasing hormone (GnRH), and the like, and specifically, for example, gonadotropin releasing hormone (GnRH), pregnant mare's serum gonadotropin (PMSG), human menopausal gonadotropin (hMG), human chorionic gonadotropin (hCG), luteinizing hormone-releasing hormone (LHRH), follicle-stimulating hormone (FSH), and the like. The amount and time period of the ovulation-inducing agent administered can be appropriately selected depending on the weight of the individual, the kind of the ovulation-inducing agent used, within the range in which the ovulation-inducing effects are exhibited.

It is desired that the monkey ovum used in the step (a) described above is mature and at the MII stage, and that the cytoplasm of the ovum is homogeneous and elastic. Such properties can be evaluated by observing the process of the intracytoplasmic sperm injection or in vitro fertilization.

The ovum collection under laparoscopic observation can be carried out as specifically described below: The amount 1.8 to 3.65 mg of gonadotropin releasing hormone (GnRH) is administered subcutaneously to 5 to 15 year-old females of *Macaca fuscata* or 4 to 15 year-old females of *Macaca fascicularis*. Two weeks after the administration of GnRH, 25 IU/kg of pregnant mare's serum gonadotropin (PMSG), 10 IU/kg of human menopausal gonadotropin (hMG) or 3 IU/kg of follicle-stimulating hormone (FSH) is administered intramuscularly once a day at a given time for consecutive 9 days. Four to five days after the administration, the ovaries are observed using a laparoscope (outer diameter: 3 mm), thereby confirming whether the ovarian follicles develop or not. Here, whether the ovarian follicles develop or not is evaluated using as an index the fact that a plurality of bodies with slightly swollen albuginea are formed in the ovary, whereby the ovary as a whole is enlarged and the uterus becomes reddish. Subsequently, PMSG, hMG or FSH is administered for 9 days. After confirming sufficient development of the ovarian follicles, 400 IU/kg of human chorionic gonadotropin (hCG) is once administered intramuscularly. Thirty-eight to forty-two hours after the administration of hGC, ovum collection is carried out. The ovum collection is carried out by puncturing the ovarian follicles, and aspirating to collect ova together with follicular fluid using a 2.5 ml injection syringe equipped with a 60 mm 19 G or 20 G Cathelin needle, wherein the syringe contains α-MEM solution containing about 0.5 ml of 10% SSS (serum substitute supplement), under laparoscopic observation (outer diameter: 10 mm). Immediately after the collection, mature ova each enveloped by cumulus oophorus cells are separated under a stereoscopic microscope, and transferred into TALP solution containing 0.3% BSA. The ovum used for fertilization can be obtained by preculture of the above mature ova for 3 to 4 hours under the conditions at 37° C. in an atmosphere consisting of 5% $CO_2$, 5% $O_2$ and 90% $N_2$.

Also, a monkey sperm may be obtained from the epididymis, or obtained by an electric stimulation. The electric stimulation includes the rectal method and the penile method, each described in Examples below, and the like. Specifically, these methods are as follows:

Rectal Method

A male monkey is anesthetized with an anesthetic as represented by ketamine hydrochloride, xylazine hydrochloride and the like, and placed in the supine position. Keratin cream is applied to a rod-shaped rectal electrode connected to an electric stimulator, and the electrode is gently inserted into the rectum of the monkey. The electric stimulator is set at an alternating voltage of 5 to 20V. The electricity is applied intermittently, thereby collecting sperms from the tip of the penis.

Penile Method

The limbs of a male monkey are held on the front face of a cage under no anesthesia, and placed at a position in which the penis is easily supported. An electrode is set to the penis and connected with a clip to an electric stimulator. The electricity is applied intermittently, thereby collecting sperms from the tip of the penis.

It is desired that the monkey sperm used in the step (a) described above is activated from the viewpoint of high fertilities. The sperm can be activated, for instance, by treatment with an agent such as caffeine, dbC-AMP, forskolin and pentoxyfylline. Among the agents, a combination of caffeine and dbC-AMP is suitable from the viewpoints of active mobility with forward mobility, and the survival rate. In addition, after the treatment of sperm with the above-mentioned agent, a sperm with even higher fertilities may be obtained by the Swim up method. There can be exhibited excellent effects that a high fertilization rate can be obtained by activating the sperm, and that fertilization can be highly efficiently achieved by intracytoplasmic sperm injection even in the case of using a sperm which is poor in mobility without the treatment.

It is desired that the amounts of caffeine and dbC-AMP used are 10 μM to 1 mM per $1\times10^7$ sperms from the viewpoint of activating the mobility.

The above-mentioned Swim up method is a method comprising collecting sperms in a round-bottomed tube by centrifugation, adding thereto a medium (about 0.5 ml) containing caffeine and dbC-AMP, allowing the cells to stand in an incubator at 37° C. under 5% $CO_2$, and the collecting sperms which have swum up after about 30 to 60 minutes.

The activation of a sperm can be evaluated by using as an index the presence of active mobility with forward mobility.

The monkey sperms can be activated, for instance, by the method described as follows:

Sperms are transferred to a tube together with a lyophilizer from a straw in which sperms obtained from the epididymis, or obtained by an electric stimulation have been stored. To the sperms, 10 ml of a BSA/BWW (Biggers, Whitten and Wittinghams) solution containing 1 mM caffeine and 1 mM dbC-AMP is then added. Therefore, the sperms are incubated for 30 minutes in a $CO_2$ incubator at 37° C. under 5% $CO_2$, to achieve sperm capacitation. Subsequently, the resulting products are centrifuged at 1,000 rpm (200×g) for 2 minutes, to discard supernatant. To the remaining sperms, about 0.5 to 10 ml of a fresh BSA/BWW solution containing 1 mM caffeine and 1 mM dbC-AMP is added. The resulting sperm solution is allowed to stand for 60 minutes in a $CO_2$ incubator at 37° C. The sperms swum-up are collected, and the mobility and the number of the sperms are confirmed. Here, the mobility of the sperms is evaluated by using as indices forward mobility and activeness of the sperms. By this method, sperms can be activated.

In the step (a), fertilization can be carried out by in vitro fertilization or intracytoplasmic sperm injection. In vitro fertilization can be carried out according to the method described in Torii, R. et al., [*Primates*, 41, 39–47 (2000)]. In addition, intracytoplasmic sperm injection can be carried out according to the method described in Hewitson, L. [*Human Reproduction*, 13, 3449–3455 (1998)].

In the method for producing the monkey-derived embryonic stem cell of the present invention, it is preferable that a culture medium selected from the group consisting of TALP (Tyrode-Albumin-Lactate-Pyruvate) solution, TALP-HEPES solution and BWW solution is used for performing the in vitro fertilization or intracytoplasmic sperm injection mentioned above, from the viewpoint of reducing the influence on the ovum. TALP solution and TALP-HEPES solution can be prepared as follows:

are prepared, and each of the reagents obtained is sterilized by filtration through a filter.

On the other hand, immediately prior to the preparation of TALP/HEPES solution,

| sodium pyruvate | 0.1 mM | 0.0011 g (per 100 ml) |
|---|---|---|
| BSA | 3 mg/ml | 0.3 g | are prepared, and each of the reagents obtained are sterilized by filtration through a filter.

Incidentally, when TALP-HEPES solution is prepared, 50 ml of NaCl and Na-HEPES (N-2-hydroxyethylpiperazine-N'-2-ethane sulfonate), phenol red and penicillin G are previously dissolved. To the resulting solution, defined amounts of the respective stock solutions are added, and the NaCl stock solution is finally added to make up a volume of 100 ml. The pH of the resulting solution is then adjusted to pH 7.4 with 1 M NaOH. The stock solution of sodium lactate is prepared by mixing an undiluted solution (60% syrup) with water in a ratio of 1:35. Phenol red is added at a concentration of 1 mg/ml to the resulting mixture. Thereafter, the pH of the resulting solution is adjusted to pH 7.6 with 1 M NaOH. Subsequently, the solution is sterilized by filtration. The reagent obtained is storable at 4° C. for one week. Twenty-eight milligrams of $NaHPO_4 \cdot H_2O$ is dissolved in 10 ml of a solution of glucose, and sterilized by filtration. The solution obtained is storable at 4° C. for one week.

Next, the composition of BWW (Biggers, Whitten and Wittinghams) solution is shown in Table 2.

TABLE 1

| Reagent | Stock Solution (mM) | Stock Solution (g/100 mol) | Final Solution (mM) | Stock Solution (ml) TALP | Stock Solution (ml) TALP-HEPES |
|---|---|---|---|---|---|
| HEPES | — | — | 10.0 | — | 240 ml |
| NaCl | 157.0 | 0.92 | 114.0 | to 100 ml | to 100 ml |
| KCl | 166.0 | 1.24 | 3.16 | 1.9 | 1.9 |
| $CaCl_2$ | 120.0 | 1.76 | 2.0 | 1.7 | 1.7 |
| $MgCl_2 \cdot 6H_2O$ | 120.0 | 2.44 | 0.5 | 0.41 | 0.41 |
| Sodium Lactate | 150.0 | — | 10.0 | 6.7 | 6.7 |
| Water | — | — | — | — | 7.1 |
| $NaH_2PO_4 \cdot H_2O$ | 20.5 | — | 0.35 | 1.7 | 1.7 |
| Glucose | 295.0 | 5.31 | 5.0 | | |
| $NaHCO_3$ | 167.0 | 1.40 | 25.0 (TALP) 2.0 (TALP-HEPES) | 15.0 | 1.2 |

Penicillin G (10,000 units/100 ml) and Phenol Red (1 mg/100 ml)

The stock solutions are sterilized by autoclave and then stored.

Here, immediately prior to the preparation of TALP solution,

| sodium pyruvate | 0.5 mM | 0.0055 g (per 100 ml) |
|---|---|---|
| gentamycin sulfate (10 mg/ml) | 50 µg/ml | 50 µl |
| BSA | 3 mg/ml | 0.3 g |

TABLE 2

| Reagent | Amount * (mg) |
|---|---|
| Sodium Chloride | 2,770 |
| Potassium Chloride | 178 |
| $KH_2PO_4$ | 81 |
| Magnesium Sulfate | 147 |
| $NaHCO_3$ | 1,053 |
| Sodium Pyruvate Salt | 14 |
| D(+)-Glucose (anhydrous) | 500 |

TABLE 2-continued

| Reagent | Amount * (mg) |
| --- | --- |
| Penicillin G | 31 |
| Streptomycin | 25 |
| DL-Sodium Lactate | 1,037 |
| Calcium Lactate | 263 |
| Phenol Red 1 mg Merk | 1 |

* :/1500 ml

The surface of the solutions used for in vitro fertilization or intracytoplasmic sperm injection can be covered with a mineral oil or the like. As a result, there can be obtained effects that drying an ovum solution or a sperm solution is avoided, and that changes in temperature, pH, concentrations of $CO_2$ and $O_2$ are avoided.

In addition, in the step (a), it is preferable that a culture medium selected from the group consisting of TALP solution, TALP-HEPES solution and BWW solution is used during fertilization from the viewpoint of reducing the influence on the ovum.

Whether fertilization is achieved or not can be evaluated by visual observation under a phase-contrast inverted microscope by using as an index the presence of two pronuclei.

An example of in vitro fertilization or intracytoplasmic sperm injection performed in the present invention is shown below.

In vitro Fertilization

One to five ova each enveloped by cumulus oophorus cells are placed in a mineral oil-covered drop of a 50 μl BSA/BWW solution on a plastic dish. A suspension of sperms is then transferred into the drops at $5.0 \times 10^5$ to $1.0 \times 10^6$ sperms/ml. The drops are covered with a mineral oil, and insemination is then carried out.

Intracytoplasmic Sperm Injection (i) Preparation of Ovum

The oocytes collected are gathered in a spot of a 50 μl TALP solution containing 0.3% BSA (BSA/TALP solution), which is covered with a mineral oil (Sigma Chem. Co.), and precultured for about 2 to 4 hours under the conditions of 37° C., 5% $CO_2$, 5% $O_2$ and 90% $N_2$.

The state of maturation of ovum can be evaluated by removing the cumulus oophorus cells by treatment with 0.1% hyaluronidase, to thereby collect an ovum, and classifying the resulting ovum into the following 4 classes, Class-1 to 4, under an inverted microscope.

Class-1: Mature ovum with a polar body (PB)

Class-2: Ovum being on maturation in which no PB and the germinal vesicle (GV) is observed Class-3: Immature ovum in which the GV is observed Class-4: Ovum with considerably deformed shape, or ovum showing denaturation or retrogressive changes in the cytoplasm An ovum classified in Class-1 is subjected to intracytoplasmic sperm injection immediately after the evaluation. An ovum classified in Class-2 or Class-3 is further gathered in a spot of a 50 μl BSA/TALP solution, which is covered with a mineral oil, and continued to be cultured under the conditions of 37° C., 5% $CO_2$, 5% $O_2$ and 90% $N_2$. In this case, the state of maturation of the ova is confirmed in the same manner as in the above. It is desired that an immature ovum and ovum classified in Class-4 are not used for fertilization.

(ii) Preparation of Sperms

The sperms are prepared in the same manner as in the in vitro Fertilization.

(iii) Intracytoplasmic Sperm Injection

The intracytoplasmic sperm injection is carried out under an inverted microscope equipped with a micromanipulator.

Spot 1:15 μl of a dilution of sperms, Spot 2:3 spots of a 5 μl 10% polyvinylpyrrolidone PBS culture medium [PVP: average molecular weight: about 360,000], and Spot 3:3 spots of a 5 μl TALP-HEPES solution (final concentration: 3 mg/ml BSA) for manipulation of ovum are sequentially placed in a dish of 150 mm in diameter, and thereafter their surfaces are covered with a mineral oil to avoid being dried. The spots are used for the working field for intracytoplasmic sperm injection. Incidentally, when the temperature for manipulation is kept constant, a heating stage may be used, if necessary.

An injection needle is connected to an ALCATHEL syringe of highly working performance. The injection needle includes a 30-degree inclined needle for human intracytoplasmic sperm injection.

An ovum supporting needle includes the above-mentioned 30-degree inclined needle for human intracytoplasmic sperm injection, and a needle having an outer diameter of about 100 μm and an inner diameter of the tip of about 15 μm, which is made of a magnetic plur (PN-30, manufactured by Narishige). The ovum supporting needle is used in the state where the needle is connected to an injector equipped with a 2000-μl airtight syringe.

Regarding the sperm, a sperm having mobility selected to be aspirated in Spot 1 on the basis of the criteria for human intracytoplasmic sperm injection, and thereafter the sperm obtained is transferred and discharged to Spot 2. In Spot 2, the mobility of the sperm is lowered due to the viscosity of PVP. The tail of sperm was rubbed with the needle to partially destroy the membrane, thus, stopping sperm movement. The sperm is aspirated together with a highly viscous solution, and transferred to Spot 3.

The mature ovum is placed in Spot 3, and immobilized at a 6-o'clock or 12-o'clock position in a clock using a supporting needle, while paying attention to avoid the destruction of the chromosome under the polar body by the injection needle. Subsequently, the sperm is placed in the tip of the injection needle, and injected into an ovum. After confirming that the needle is passed through the zona pellucida, the oolemma is aspirated. After confirming the rupture of the membrane, the contents (the sperms and the oosome) in the injection needle are injected. A series of the manipulations for injecting a sperm and oosome are repeated. Two or three ova are subjected to intracytoplasmic sperm injection in a single manipulation. When the inner surface of the tip of the needle is contaminated with sperms and oosome, the surface is washed with Spot 2.

After the step (a), step (b) of allowing the fertilized ovum obtained in the step (a) to differentiate into a blastocyst by in vitro culture is carried out.

The in vitro culture includes a micro-hanging drop culture characterized in that a culture medium is covered with a mineral oil from the viewpoint of avoiding drastic changes in temperature and carbon dioxide gas concentration. The micro-hanging drop culture is a technique which is not usually employed in experiments for humans, but widely employed in the experiment for laboratory animals such as mouse and rabbit. According to this culture method, there can be exhibited an excellent effect that an unexpectedly high development rate by applying the method in the development of a monkey-derived blastocyst.

For culturing a fertilized ovum, it is desired that the door of an incubator should not be opened and the incubator is tightly closed for 7 to 9 days, preferably 8 days after starting the cultivation in the case of in vitro fertilization, and 7 to 10 days, preferably 9 days after starting the cultivation in the case of intracytoplasmic sperm injection, until the appearance of blastocyst is expected, from the viewpoint of avoiding unwanted stress, such as changes in temperature and pH which can be caused during observation of the culture process.

The appearance of blastocyst tends to be proportional to the rate of early stage of cell division.

In addition, one of the significant features resides in culture medium, culture temperature and culture atmosphere which are utilized in the in vitro culture in the step (b).

It is preferable in the step (b) that the in vitro culture is performed by using CMRL-1066, TCM-199, DMEM, α-MEM, or the like. It is especially preferable that in vitro culture is performed using CMRL-1066. Incidentally, CMRL-1066 can be prepared as follows:

The amount 0.014615 g (1 mM) of L-glutamine is dissolved in 10 ml of Solution A [penicillin G (1000 units), 0.5 ml of gentamycin sulfate (10 mg/ml), 10 ml of CMRL-1066 (10×) (without $NaHCO_3$ and L-glutamine), 0.218 g of $NaHCO_3$, 6.7 ml of sodium lactate (290 mOsmol's stock), added with water to a volume of 100 ml]. The resulting solution is then sterilized by filtration. To 1 ml of the solution after the sterilization is added 9 ml of Solution A, to give Solution B in a total volume of 10 ml. The amount 0.0055 g (final concentration: 5 mM) of sodium pyruvate is added to and dissolved in Solution B, to give Solution C. Eight milliliters of Solution C and 2 ml of BCS (bovine calf serum) are mixed. The resulting mixture is sterilized by filtration, to give a solution of CMRL-1066.

Further, as the culture medium, it is desired that a culture medium selected from the group consisting of TALP solution, TALP-HEPES solution and BWW solution is used from the viewpoint of reducing the influence on the ovum. Specifically, the culture medium mentioned above includes a culture medium in which TALP and CMRL-1066 are used in combination. According to the culture medium in which TALP and CMRL-1066 are used in combination, there are some advantages in that by using the culture medium after confirmation of the fertilization allows the morula to develop into blastocyst, and to achieve extremely high developmental ratio of 40 to 46% in fertilized embryo.

It is desired that the culture temperature is 37° C. or higher, preferably 37.5° C. or higher, and that the culture temperature is 38.5° C. or lower, preferably 38.2° C. or lower, from the viewpoint of shortening the time required in the development, and the viewpoint of promoting of development from morula into blastocyst. Specifically, at 7 days after in vitro fertilization, and at 8 days after intracytoplasmic sperm injection, blastocysts can be efficiently obtained by culturing at 38° C.

The culture atmosphere is preferably a low-oxygen atmosphere from the viewpoint of promoting or improving the development from morula to blastocyst. Specifically, by using an atmosphere consisting of 5% $CO_2$, 5% $O_2$ and 90% $N_2$, which is lower in $O_2$ concentration than a culture atmosphere usually employed for preparation of ES cells, there can be exhibited excellent effects such that blastocysts can be obtained surprisingly efficiently.

Further, step (c) of establishing an embryonic stem cell line using the blastocyst obtained in the step (b) is carried out. In the step (c), the embryonic stem cell line is established by culturing the inner cell mass derived from the blastocyst obtained in the step (b) on feeder cells or in the presence of leukemia inhibitory factor [LIF, also referred to as differentiation inhibitory factor (DIF)].

When inner cell mass is obtained from a blastocyst, blastocysts in which the zona pellucida has been removed may be used. The zona pellucida may also be removed by treating with hyaluronidaze, pronase, acidic Tyrode's solution and the like. When the zona pellucida is removed by hyaluronidaze, pronase, acidic Tyrode's solution and the like, blastocysts may be incubated in M2 culture medium containing an appropriate concentration of hyaluronidaze, pronase, acidic Tyrode's solution or the like [see, e.g., D. M. Glover et al., ed., *DNA Cloning* 4, *Mammalian Systems, A Practical Approach* 2nd edition (1995), and the like]. After removing the zona pellucida, the blastocysts obtained may be washed with phosphate-buffered saline, if necessary.

In order to separate the inner cell mass from a blastocyst without the zona pellucida, for instance, the blastocyst may be subjected to immunosurgery. Further, endodermal cells are stripped away by pipetting. The resulting inner cell mass obtained is cultured on feeder cells for 1 week. The proliferated inner cell mass is trypsinized (for instance, treated with 0.25% by weight of trypsin+0.5 mM EDTA, and the like), to obtain a mass made of about 3 to 4 cells. Further, these cells are cultured again on feeder cells.

The anti-serum used in the immunosurgery includes, for example, a rabbit anti-monkey serum, particularly a rabbit anti-Japanese monkey serum, a rabbit anti-cynomolgus monkey serum and the like. The inner cell mass can be separated by transferring the blastocysts into a solution prepared by 20-fold diluting the anti-serum with M16 culture medium [see *DNA Cloning* 4, *Mammalian Systems, A Practical Approach*, supra, and the like], and incubating them at 37° C. for 30 minutes. In addition, the trophectoderm may be physically removed under a microscope using a glass needle, as required.

The feeder cell includes a cell obtained by treating with mitomycin C or irradiating with X ray, and the like a fibroblastic primary cell culture derived from a murine fetus at Day 12 to Day 16 from pregnancy, murine fetal fibroblast cell line, STO cell, and the like. The mouse-derived feeder cells are advantageous for experiments in that they can be prepared in a large scale.

The preparation of a feeder cell can be carried out, for instance, by the method described in Examples below, and the like.

The feeder cells are plated to a gelatin-coated culture vessel using MEM (minimum essential medium eagle) medium. The feeder cells may be plated on a culture plate to an extent that the cells cover the surface of the plate without spacing.

The inner cell mass is plated on feeder cells after exchanging MEM medium with a medium for culturing ES cells [ES cell culture medium, Table 3], in a culture vessel in which the feeder cells are plated,.

TABLE 3

Composition of ES Cell Culture Medium

| Name of Manufactural Product | Amount Added |
| --- | --- |
| DMEM/F12 (manufactured by Sigma) | 500 ml |
| FBS (manufactured by JRH BIOSCIENCES) | 75 ml |
| Glutamine (manufactured by Sigma; 200 mM) | 5 ml |

TABLE 3-continued

Composition of ES Cell Culture Medium

| Name of Manufactural Product | Amount Added |
|---|---|
| Mixture of Penicillin (manufactured by Sigma; 10,000 IU/ml) and Streptomycin (manufactured by Sigma; 10 mg/ml) | 5 ml |
| Sodium Pyruvate (manufactured by Sigma; 100 mM) | 5 ml |
| Sodium Hydrogencarbonate (manufactured by Sigma; 7.5%) | 8 ml |
| 2-Mercaptoethanol (manufactured by Sigma; final concentration: $10^{-4}$ M) | 4 µl |
| LIF (manufactured by ESGRO; final concentration: 1000 U/ml) | 0.5 ml of one having $10^6$ U/ml |

The culture conditions for the cells may be the conditions utilized usually for a culture condition of mouse ES cells. For instance, the cells may be cultured for 7 days under the conditions at 37° C. in 5% $CO_2$. Incidentally, it is desired that the culture medium is not exchanged for 3 days after starting the culture and that the state of implantation is observed every day under a microscope, from the viewpoint of avoiding the prevention of implantation of inner cell mass. In addition, the cells may be sequentially transferred to a larger plate for subculture as the cells proliferate.

Next, the embryonic stem cells are identified and evaluated. Incidentally, the exemplary evaluation criteria are as follows.

EXAMPLES OF EVALUATION CRITERIA

Karyotype
The chromosome number is not abnormal. Typically, whether or not the chromosome number is the same as that of the original monkey (2n=42) is determined.

Pluripotency
For instance, the potential to differentiate can be examined by injecting cells ($1\times10^5$ to $1\times10^6$ cells), which are appeared to be embryonic stem cells, to hypodermis, the renal capsule or in the testis of a 8–12 week old SCID mouse or nude mouse, examining the presence or absence of the tumor formation at 5 to 16 weeks after the injection, wherein when tumors are formed, the tumors are subjected to the histological test. Also, various types of potentials to differentiate can be determined and the pluripotency can be evaluated by removing the feeder cells or by adding a differentiation-inducing agent such as retinoic acid.

Morphological Features
1. There are exhibited high nucleus/cytoplasm ratio, conspicuous nucleoli, and colonization.
2. The colonies are more flat, as compared to the mouse ES cell colonies.

Figure 1:
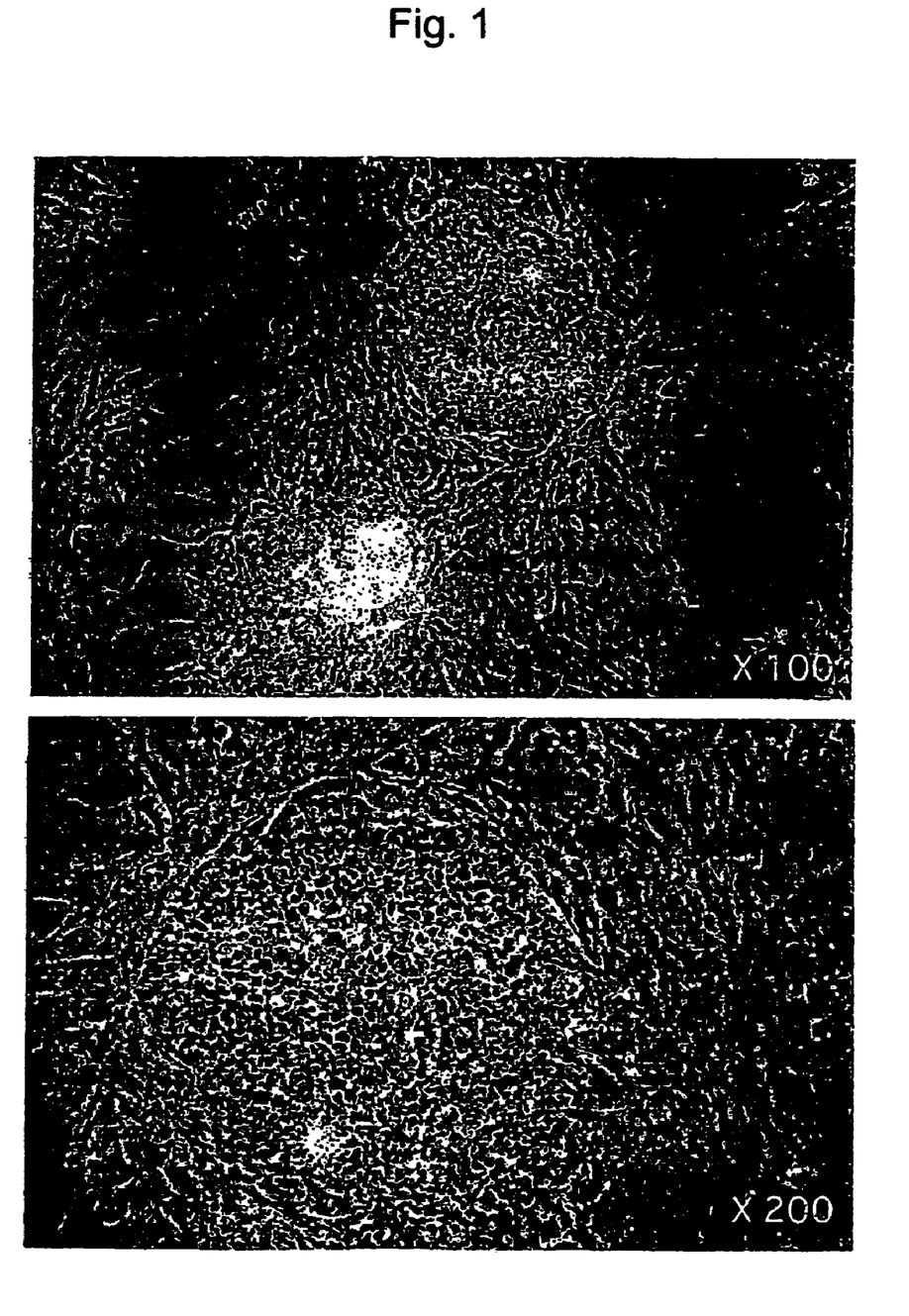
FIG. 1 is a photograph showing the results of microscopic observation of the cynomolgus monkey-derived embryonic stem cells of the present invention. The upper panel shows the results of observation at a low magnification (100×), and the lower panel shows the results of observation at a high magnification (200×).
Figure 2:
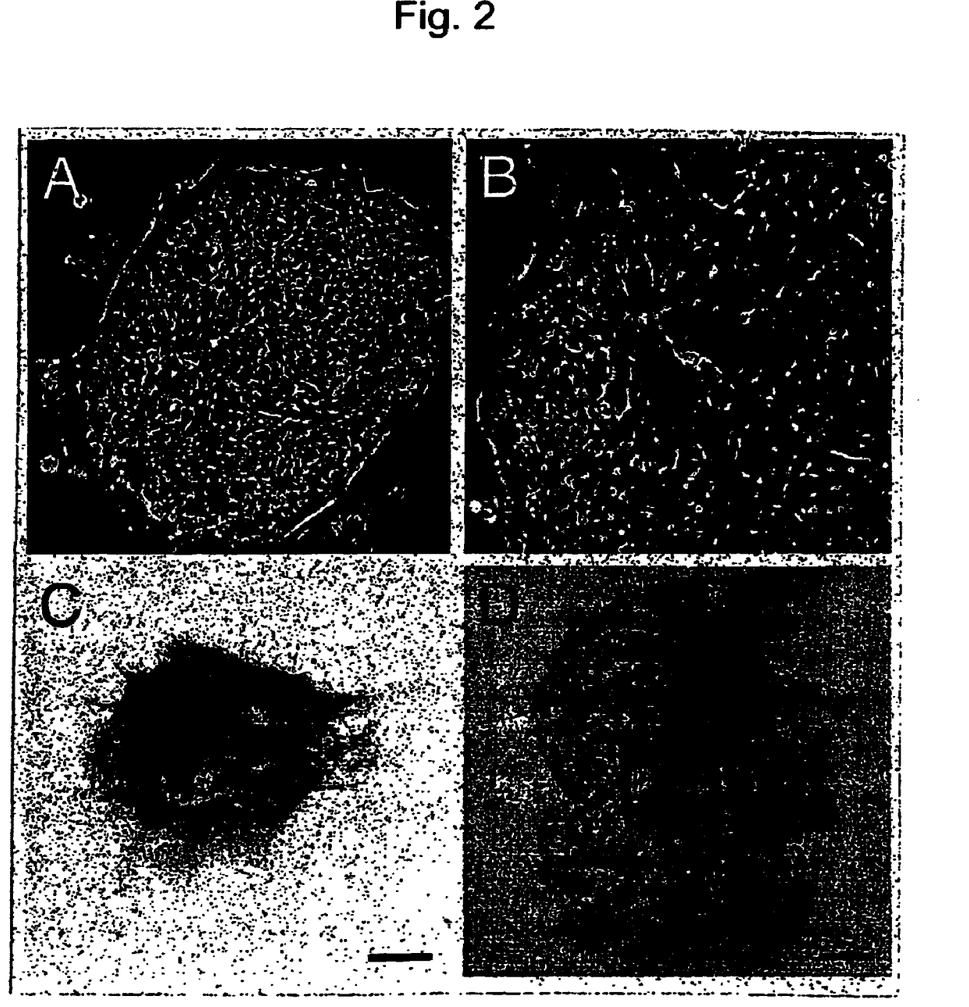
FIG. 2 is a photograph showing the results of observation of the cynomolgus monkey-derived embryonic stem cells of the present invention by various techniques. Panel A and Panel B respectively show the results of microscopic observations of the cynomolgus monkey-derived embryonic stem cells of the present invention [Panel A: low magnification (Bar=100 µm), Panel B: high magnification (Bar=50 µm)]. Panel C shows the results of microscopic observation of the cynomolgus monkey-derived embryonic stem cells of the present invention after alkaline phosphatase staining (Bar=100 µm). Panel D shows the results of microscopic observation of the cynomolgus monkey-derived embryonic stem cells of the present invention after immunostaining for SSEA-4 (Bar=100 µm).

Examples of the morphological features are shown in Panel A and Panel B in FIG. 1 and FIG. 2.

Expression of Cell Surface Markers
Negative Control: SSEA-1
Positive Control: SSEA-3, SSEA-4

The respective cell surface markers above are glycolipid cell surface markers which are stage-specific embryonic antigens. The markers can be detected by a conventional immunostaining or the like using antibodies raised against these markers as antigens.

Alkaline Phosphatase Activity
The alkaline phosphatase activity can be detected by a conventional alkaline phosphatase staining.

Specifically, the monkey-derived embryonic stem cell of the present invention includes an established cynomolgus monkey-derived cell, specifically an embryonic stem cell, having the following properties:
(i) being capable of indefinitely proliferating while being maintained in an undifferentiated in state;
(ii) having the same chromosome number as that of original *Macaca fascicularis*;
(iii) exhibiting the pluripotency when transplanted to hypodermis, the renal capsule or the testis of a 8–12 week-old SCID mouse or nude mouse;
(iv) being negative for SSEA-1 and positive for SSEA-3 and SSEA-4; and
(v) exhibiting an alkaline phosphatase activity.

The cynomolgus monkey-derived embryonic stem cell has the following morphological features: (vi) exhibiting high nucleus/cytoplasm ratio, conspicuous nucleoli, and colonization, and being more flat colonies compared to the mouse ES cell colonies (see, for example, Panel A and Panel B in FIG. 1 and FIG. 2).

The established cynomolgus monkey-derived embryonic stem cell of the present invention exhibits the ability to differentiate into ectodermal cells, mesodermal cells, endodermal cells and the like, more specifically the ability to differentiate into, for example, neuron, glia, muscle, cartilage, bone, ciliated epithelium, intestinal epithelium and the like, when transplanted to hypodermis, the renal capsule or the testis of a 8–12 week-old SCID mouse or nude mouse.

The established cynomolgus monkey-derived embryonic stem cell of the present invention is expected to be used for generating model animals of diseases and for preparing tissues for transplantation.

The monkey-derived embryonic stem cell of the present invention allows the screening of a reagent for specific differentiation into a tissue or a cell, especially preferably of a primate tissue or a primate cell. The present invention encompasses a method for screening a reagent for specific differentiation into a tissue or a cell.

One of the features of the method for screening a reagent for specific differentiation into a cell or tissue of the present invention resides in that the embryonic stem cell of the present invention is kept in the presence of a test substance.

In the screening method of the present invention, since the embryonic stem cell of the present invention is used, there are exhibited excellent effects that the reagent useful for embryological studies, studies of diseases and clinical applications and useful for obtaining the desired differentiated cells or differentiated tissues can be screened.

In the screening method of the present invention, the specific differentiation from an embryonic stem cell into the desired tissue or cell can be evaluated by, for example, using as an index a marker expressed in the desired tissue or cell. The marker for the desired tissue or cell includes tissue- or cell-specific antigens. The marker for the desired tissue or cell includes, for example, neuron-specific enolases, glia fibrous acidic proteins, nestin and the like as a marker for a neuronal cell; S-100 protein, tartaric acid-resistant acid phosphatase and the like as a marker for cartilage; desmin, muscle-specific actin and the like as a marker for muscle. Such specific marker may be detected by conventional ELISA, immunostaining or the like using antibodies against the markers, or detected by conventional RT-PCR, DNA array hybridization or the like using a nucleic acid encoding the marker. Incidentally, the term "nucleic acid" refers to genomic DNA, RNA, mRNA or cDNA.

The reagent obtained by the screening method is encompassed by the present invention. According to the reagent, applications in the field of regenerative medicine are expected.

In addition, the differentiated cell and differentiated tissue each differentiated from the embryonic stem cells of the present invention are also encompassed by the present invention.

The differentiated cell and differentiated tissue can be identified by observing the expression of the markers specific for the cell or tissue, or the morphological features.

The differentiated cell or differentiated tissue of the present invention is a cell or tissue of monkey which is closely related to humans. Therefore, the cell or tissue is suitably used as a subject in a variety of tests for various agents, or to use as a model for transplantation of tissue or cell.

The present invention will be more specifically described below by the following Examples and the like, but is not limited to the Examples. Here, "%" as used in the Examples and the like indicates % by weight, unless otherwise specified. Also, the expression "%" for $CO_2$, $O_2$ and $N_2$ indicates % by volume.

Example 1

Method for Preparing Blastocyst from Cynomolgus Monkey

In a monkey, unlike in other laboratory animals such as a mouse, a rat and a rabbit, a method for collecting a fertilized ovum by perfusion of an oviduct or uterus remains yet to be established in the current situation. It has been also known that the efficiency of a method for collecting a fertilized ovum from the uterus in the ovulation cycle is very low.

Therefore, at this time, in order to produce a blastocyst suitable for the establishment of an embryonic stem cell, there was investigated a method comprising carrying out fertilization by in vitro fertilization and intracytoplasmic sperm injection, and developing to a blastocyst by in vitro culture.

(1) Ovary Stimulation Method

To a female cynomolgus monkey (4–15 year-old), 1.8 mg of gonadotropin-releasing hormone (GnRH) [trade name: Leuplin, manufactured by Takeda Chemical Industries, Ltd.; or trade name: Sprecur, manufactured by Hoechst Marion Roussel] was subcutaneously administered. Starting at 2 weeks after GnRH administration, 25 IU/kg pregnant mare's serum gonadotropin (PMSG) [trade name: Serotropin, manufactured by Teikoku Hormone Manufacturing, Co., Ltd.], 10 IU/kg human menopausal gonadotropin (hMG) [trade name: Pergonal, manufactured by Teikoku Hormone Manufacturing, Co., Ltd.] or 3 IU/kg follicle-stimulating hormone (FSH) [trade name: Fertinorm, manufactured by Serono Laboratories] was intramuscularly administered at a given time in the evening once a day for nine consecutive days, in this Example. Five days after the administration, the ovary was observed by using a laparoscope (3 mm in outer diameter), thereby confirming the presence or absence of follicle development.

Subsequently, after confirming sufficient follicle development by administration of PMSG, hMG or FSH, 400 IU/kg human chorionic gonadotropin (hCG) [trade name: Pubero-gen, manufactured by Sankyo Co., Ltd.] was administered once intramuscularly. Forty hours after hCG administration, ova were collected.

The ovum collection was carried out by puncturing the ovarian follicles, and aspirating to collect ova together with follicular fluid under a laparoscope observation (10 mm in outer diameter) using a 2.5 ml injection syringe equipped with a 60 mm 19G or 20G Cathelin needle, wherein the syringe contains a solution of α-MEM (alpha-modification of Eagles Medium, manufactured by ICD Biomedical Inc.) containing about 0.5 ml of 10% SSS (serum substitute supplement, manufactured by Irvine Scientific Sales Inc.).

After the collection, a mature ovum enveloped by cumulus oophorus cells was immediately separated under a stereoscopic microscope, transferred to TALP containing 0.3% BSA (hereinafter referred to as BSA/TALP), and pre-cultured for 3 to 4 hours in a carbon dioxide incubator at 37° C., 5% $CO_2$, 5% $O_2$ and 90% $N_2$.

As described above, the ovum collection under laproscopic observation was carried out by making only about 1 cm incision in the abdominal wall, inserting a laparoscope and puncturing the ovary through the abdominal wall.

On the other hand, the ovum collection method was performed by the ovarian extirpation method comprising extirpating ovary and uterus, and thereafter perfusing uterine tube, in the case of a mouse, or by the ovarian puncture method using ultrasonic diagnostic equipment, in the case of human. In the case of a monkey, however, the ovarian extirpation method is inapplicable in some cases because of the limited number of individuals. In addition, since a monkey is smaller in body size than human, it is extremely difficult to apply the method using ultrasonic diagnostic equipment. For these reasons, a method for collecting an unfertilized ovum for in vitro fertilization of a monkey, both at domestically and abroad, are usually performed by the ovarian puncture method under direct vision of the ovary by laparotomy. However, this method has drawbacks such as ① larger burden on an individual, ② much time consumption for postoperative wound healing, and ③ major risk of infection.

In contrast, the method employed in the present Example provides even magnified views compared to the case of the direct vision. It is therefore possible to collect ova with the puncture site targeted accurately. In addition, since the operation can be completed in a very short time by suturing a single stitch for the abdominal wall after ovum collection, it was found that the present method is very useful from the viewpoint of animal welfare.

(2) Collection of Sperm (i) Collection Method from Epididymis

Immediately after collecting the epididymis of a male cynomolgus monkey (10–15 year-old), a 1 ml injection syringe equipped with a 23G needle was inserted to the seminal duct. Thereafter, BWW containing 0.3% BSA (hereinafter referred to as BSA/BWW) was injected slowly, thereby collecting the semen overflowed from the tail of the epididymis cut.

(ii) Collection Method by Electric Stimulation i) Rectal Method

A male cynomolgus monkey (10–15 year-old) was anesthetized with a combination of ketamine hydrochloride and xylazine hydrochloride (5 mg/kg and 1 mg/kg, respectively) and placed in the supine position. Keratin cream was applied to a rod-shaped rectal electrode connected to an electric stimulator. Thereafter, the electrode was gently inserted to the rectum of the monkey. The penis was washed with sterile physiological saline and wiped with paper towel or the like. The penis tip was immersed in a test tube (50 ml). Subsequently, the electricity was conducted by setting the electric stimulator to an alternating voltage of 5 V. The electricity was conducted for 3 to 5 seconds and then paused for 5 seconds. This procedure was repeated in up to three cycles. If ejaculation was observed, stimulation was terminated at that time. If ejaculation was not observed, the same procedure was performed by changing the voltage to 10 V. If ejaculation was still not observed, the procedure was carried out at 15 V and 20 V.

ii) Penile Method

Under no anesthesia, the four limbs of a male cynomolgus monkey (10–15 years old) were held on the front face of a cage and placed at a position that the penis is easily supported. The operator, wearing surgical rubber gloves, washed the monkey's penis with sterile physiological saline and wiped with paper towel or the like. An electric stimulator was provided and thereafter, an electrode was set to the penis and connected with a clip to the stimulator. The electricity was conducted by repeating the procedure of ON-OFF at 1-second intervals at a direct current voltage of 5 V while shortening the interval gradually with the passage of time. If ejaculation was not observed, the same procedure was performed at a voltage of 10 V, 15 V, and 20 V. If ejaculation was still not observed, the same procedure was performed with an alternating current.

(3) Treatment after Semen Collection and Cryopreservation (Torii et al., 1998)

The semen collected by the rectal method or the penile method was allowed to stand for about 30 minutes in a carbon dioxide incubator at 37° C. A sperm solution was prepared by collecting only a liquid component, and adding thereto about 1 to 2 ml of BWW containing 0.3% BSA (Biggers, Whitten and Wittinghams) (BSA/BWW). Thereafter, the resulting solution was gently overlaid on a layered liquid of 2.5 ml of 80% Percoll (manufactured by American Permacia Biotech Inc.) and 2.5 ml of 60% Percoll. After centrifugation of the resulting product at 1,400 rpm and at room temperature for 20 minutes, the upper layer was aspirated off with about 0.5 ml of the bottom portion remaining in the test tube. Further, about 10 ml of BSA/BWW was added thereto and mixed gently. After centrifugation of the mixture at 1,400 rpm and at room temperature for 3 minutes, the upper layer was aspirated off with about 0.5 ml of the bottom portion left in the test tube.

An appropriate amount of BSA/BWW was added to the sperm fraction so as to reach a sperm count of about $5 \times 10^7$ to $1.0 \times 10^8$ cells/ml, to prepare a sperm solution. Thereafter, the resulting solution was allowed to stand at 4° C. for about 60 to 90 minutes. Subsequently, to the solution, a TTE-G solution [TTE medium (composition per 100 ml of the medium: 1.2 g Tes, 0.2 g Tris-HCl, 2 g glucose, 2 g lactose, 0.2 g raffinose, 20 ml egg yolk, 10,000 IU penicillin-G, 5 mg streptomycin sulfate) containing glycerol at a final concentration of 12%], in a one-fifth amount of the amount of the sperm solution, was gently added drop by drop in ice water, and thereafter, the resulting mixture was allowed to stand for 5 minutes. The above-mentioned procedures of dropping of TTE-G solution and allowing to stand were repeated in five cycles.

After allowing the resulting mixture to stand for 60 to 90 minutes in ice water, the sperm solution was placed in a 0.25 or 0.5 ml straw. The straw was kept above a vessel containing liquid nitrogen for about 5 minutes, and thereafter, it was further kept above the liquid nitrogen for 5 minutes. The straw was placed in the liquid nitrogen and stored.

(4) Preparation of Sperm for In vitro Fertilization

The straw was taken out from the liquid nitrogen, kept at room temperature for 30 seconds, and then immersed in a 37° C. hot bath for 30 seconds, to thereby thaw the stock sperm solution. Subsequently, the capacitation was carried out by adding 10 ml of BSA/BWW containing 1 mM caffeine (manufactured by Sigma Ltd.) and 1 mM dbC-AMP (manufactured by Sigma Ltd.) to the straw, and incubating the resulting mixture in a carbon dioxide incubator at 37° C. for 30 minutes.

Thereafter, the sperm solution was centrifuged at 1,000 rpm (200 g) for 2 minutes, to discard the supernatant. Subsequently, about 0.5 to 1 ml of BSA/BWW containing 1 mM caffeine and 1 mM dbC-AMP was added to the sperms. The sperm solution obtained was allowed to stand for 60 minutes in a carbon dioxide incubator at 37° C. Sperms that were swum up were collected, and confirmed for their mobility and number. Sperms for in vitro fertilization were thus obtained.

(5) Method of Fertilization

1) In vitro Fertilization

One to five ova each enveloped by cumulus oophorus cells were placed in a drop of a 50 μl BSA/BWW covered with mineral oil on a plastic dish. Subsequently, the sperm suspension was transferred to the drop to obtain a sperm density of $5.0 \times 10^5$ to $1.0 \times 10^6$ sperms/ml. After covering the drop with mineral oil, insemination was then carried out.

The fertilized ova were then incubated in a carbon dioxide incubator at 37° C., 5% $CO_2$, 5% $O_2$ and 90% $N_2$. Five hours after insemination, the BWW solution was exchanged with TALP solution, and thereafter, the ova were examined for fertilization. As a result, fertilized ova were obtained at a fertilization rate of as high as about 45%. The ova confirmed to have fertilized were cultured for about 20 hours, transferred to CMRL-1066 solution and continued to be cultured.

2) Intracytoplasmic Sperm Injection (i) Preparation of Ova

The collected oocytes were gathered in a 50 μl spot of a solution of TALP containing 0.3% BSA (BSA/TALP) covered with mineral oil (manufactured by Sigma Ltd.), and then pre-cultured for about 2 to 4 hours at 37° C. in the presence of 5% $CO_2$, 5% $O_2$ and 90% $N_2$.

To confirm the state of maturation of the ovum, the oocyte culture was exposed to a TALP-HEPES solution containing 0.1% hyarulonidase (manufactured by Sigma Ltd.) for 1 minute, and thereafter cumulus oorphorus cells were removed by pipetting. The recovered ova were classified under an inverted microscope into classes 1 through 4 as follows:

Class-1: Mature ovum with polar body (PB)
Class-2: Ovum being on maturation in which no PB and germinal vesicle (GV) are observed
Class-3: Immature ovum in which GV is observed
Class-4: Ovum with considerable deformed shape, or ovum showing denaturation or retrogressive changes in the cytoplasm.

The ovum classified in class-1 was subjected to intracytoplasmic sperm injection immediately after class confirmation. The ova classified in class-1 or class-3 were further gathered in a 50 μl spot of a BSA/TALP solution, which was covered with mineral oil, and then cultured at 37° C., 5% $CO_2$, 5% $O_2$ and 90% $N_2$. Twenty-four hours after cultivation, the state of maturation of the ovum was confirmed. The mature ovum was subjected to intracytoplasmic sperm injection at that time. The remaining immature ova and the ova each classified in class-4 were not subjected to fertilization.

(ii) Preparation of Sperm

Sperms were prepared in the same manner as in vitro fertilization.

(iii) Intracytoplasmic Sperm Injection

Intracytoplasmic sperm injection was carried out under an Olympus IX 70 inverted microscope which was equipped with a micro-manipulator manufactured by Narishige Co., Ltd.

Spot 1: 15 µl of dilution of sperms, Spot 2: 3 spots of a 5 µl 10% polyvinyl pyrrolidone PBS culture medium [PVP: average molecular weight ca. 360,000, manufactured by nacalaitesque], and Spot 3: 3 spots of a 5 µl solution of TALP-HEPES for ovum manipulation (final concentration 3 mg/ml BSA) were sequentially placed in a 150 mm dish. Thereafter, their surfaces were covered with mineral oil to avoid from being dried. This dish was used as the working field for intracytoplasmic sperm injection. In the present Example, no attention was paid to a change in operating temperature, and no heating stage was used.

As the injection needle, there was used a 30 degree inclined needle for human intracytoplasmic sperm injection (7–8 µm in outer diameter and 5–7 µm in inside diameter, manufactured by Medicon International). The needle was connected to an ALCATEL syringe of high working performance.

As the ovum supporting needle, there was used the same 30 degree inclined needle for human intracytoplasmic sperm injection or a needle about 100 µm in outer diameter and about 15 µm in tip inside diameter prepared with a magnetic plur (trade name: PN-30, manufactured by Narishige Co., Ltd.). This needle was connected to a Narishige injector equipped with a 2000 µl airtight syringe.

In Spot 1, a sperm having mobility was selected and aspirated on the basis of the Human Intracytoplasmic Sperm Injection Standard. The resulting sperm was then transferred to Spot 2 and discharged. In Spot 2, the mobility of sperm was lowered due to the viscosity of PVP. The tail of the sperm was rubbed with the injection needle to partially destroy the membrane, thus stopping sperm movement. The sperm was aspirated together with the highly viscous solution and transferred to Spot 3.

A mature ovum was placed in Spot 3 and immobilized at a 6-o'clock or 12-o'clock position using the ovum supporting needle while paying attention to avoid the destruction of the chromosome under the polar body by the injection needle. Subsequently, the sperm was placed in the tip of the injection needle and injected into the ovum. After confirming needle passage through the zona pellucida, the oolemma was aspirated. After confirming the rupture of the membrane, the contents (sperm and ovum cytoplasm) in the injection needle were injected. A series of these procedures for injection of sperms and ovum cytoplasm were repeated. Two or three ova are subjected to intracytoplasmic sperm injection in a single manipulation. When the inside of the tip is contaminated with sperms or oosome, the tip is washed with spot 2.

The ova resulting from intracytoplasmic sperm injected were returned to the incubator. The cultivation was then started at 37° C., 5% $O_2$, 5% $CO_2$ and 90% $N_2$. Immediately after intracytoplasmic sperm injection, a 50 µl spot of a CMRL-1066 solution was made on a 60 mm non-coated culture dish and covered with paraffin oil. As a general rule, equilibration between the spot and the gas phase was carried out for at least 3 hours. Twenty-four hours after intracytoplasmic sperm injection, the ovum was transferred from the TALP solution to the above-mentioned spot of CMRL-1066 solution and cultured for 8 days in a carbon dioxide incubator at 37° C., 5% $O_2$, 5% $CO_2$ and 90% $N_2$ under closed conditions. As a result, fertilized ova were obtained at a fertilization rate of as high as about 75 to 85%.

As described above, the activation of sperms was carried out prior to in vitro fertilization and intracytoplasmic sperm injection in monkey. In the cases of mouse and human, intact sperm for ordinary in vitro fertilization and intracytoplasmic sperm injection are used. However, in the Example, a sperm having higher fertility was obtained by carrying out activation with caffeine and dbC-AMP, and then employing Swim-up method, in order to achieve a higher fertilization rate. It was found that high fertilization can be achieved by employing this additional procedure in in vitro fertilization. Furthermore, the same treatment resulted in a high fertilization rate in intracytoplasmic sperm injection even with spermatozoa unsuitable for in vitro fertilization due to a lack of mobility. It was found that this method was very effective in a case where sperm of poor fertilization rate has been supplied.

(6) Method for Cultivation

In in vitro fertilization and intracytoplasmic sperm injection, the micro-hanging drop culture method by medium coverage with mineral oil, which is usually not employed in humans but widely employed in laboratory animals such as a mouse and a rabbit, was used to avoid rapid changes in temperature and carbon dioxide gas concentration during cultivation after confirmation of fertilization. In addition, to avoid unwanted stress due to changes in temperature or pH associated with examination of the course of cultivation, cultivation was carried out under closed conditions until the time when appearance of blastocysts was expected without opening or closing of the incubator door for 7 days after cultivation initiation for in vitro fertilization and 8 days after cultivation initiation for intracytoplasmic sperm injection.

The culture medium, cultivation temperature, and cultivation gas phase used here are as follows:

Culture Medium: TALP & CMRL-1066

When BWW, which is commonly used in the case of a mouse, PI (manufactured by Nakamedical, Inc.) or Blast medium (manufactured by Nakamedical, Inc.), which are commonly used in human, or newly developed HFF (human follicular fluid, manufactured by Fuso Pharmaceutical Industries, Ltd.), development progresses smoothly to the fertilization and segmentation stages but stops at the morula stage. It was found that by using in a combination of TALP culture medium and CMRL-1066 culture medium, the blastocyst as found to be developed, and that the developmental ratio was found to be an extremely high ratio of 40 to 46% in fertilized embryos. It is considered that the adverse effect on ova was reduced by the use of TALP, which is derived from HEPES buffer solution, rather than PBS, a phosphate buffer solution, in the procedures outside the incubator.

Culture Temperature: 38° C.

Embryo culture is usually carried out at 37° C. in a mouse and human. In a monkey, however, development at this temperature was slow with no development to the morula stage and thereafter. Therefore, cultivation in the present Example was carried out at a slightly higher temperature of 38° C., as compared to the case of bovines and other animals whose embryos are cultured at 38.5° C. As a result, blastocysts were obtained at 7 days after cultivation for in vitro fertilization and 8 days after cultivation for intracytoplasmic sperm injection.

Culture Atmosphere: 5% $CO_2$, 5% $O_2$ and 90% $N_2$

Although development stopped at the morula stage under the commonly used conditions of 5% $CO_2$ and 95% air, a high ratio of development into the blastocysts was observed by culturing fertilized ova at 5% $CO_2$, 5% $O_2$ and 90% $N_2$.

Example 2

Method for Establishing Monkey ES Cells (1) Preparation of Feeder Cells

Primary embryonic fibroblasts (hereinafter also referred to as PEFs) obtained from a 12.5 day-old mouse embryo were cultured for primary generation to third generation in an MEM medium containing 10% fetal bovine serum (FBS) until the cells became confluent. Subsequently, the PEFs were cultured for 2 to 3 hours in an MEM medium containing mitomycin C (MMC) at a final concentration of 10 μg/ml to inactivate cell division. The medium containing MMC was then removed. The cells were washed three times with PBS. The washed cells were trypsinized (0.05% trypsin and 1 mM EDTA), and removed from the culture dish. Thereafter, the number of the cells were counted.

The MMC-treated PEFs were plated to a gelatin-coated 24-well culture dish at $2 \times 10^4$ cells per well.

After plating actually the resulting cells onto the dish and confirming an appropriate number of the resulting cells, the mouse ES cells were cultured and their nature was examined. As a result, since the ES cells had a good ability to proliferate and were maintained in an undifferentiated condition, the cells obtained were thus shown to be suitable as feeder cells. In addition, feeder cells obtained until the third generation (primary generation to third generation) were preferred.

(2) Separation of Inner Cell Mass from Monkey Blastocysts

To remove the zona pellucida, the monkey blastocysts were transferred to an M2 culture medium [see for example D. M. Glover et al., ed., *DNA Cloning 4 Mammalian Systems—A Practical Approach—*, 2nd edition (1995), and the like] containing pronase or Tyrode at a final concentration of 0.5% and incubated at 37° C. for 10 minutes. The blastocysts with remaining zona pellucida were further treated with pronase at 37° C. for 5 minutes. After confirming the removal of the zona pellucida, the blastocysts obtained were washed twice with PBS.

Subsequently, the blastocysts were transferred to a solution prepared by 20-fold diluting rabbit anti-cynomolgus monkey lymphocyte serum with M16 culture medium [see above-mentioned DNA Cloning 4 Mammalian Systems—A Practical Approach—and the like] and incubated at 37° C. for 30 minutes. The blastocysts obtained were then washed three times with PBS. The blastocysts were transferred to a solution prepared by 50-fold diluting the complement with M16 culture medium, and incubated at 37° C. for 30 minutes. The blastocysts obtained were washed three times with PBS. If the trophectoderm of blastocysts could not be completely removed by these procedures, the trophectoderm was physically removed using a glass needle under a microscope. Inner cell mass (ICM) was thus separated.

(3) Culture of Monkey Inner Cell Mass

The MEM medium was removed from the 24-well culture dish in which the feeder cells obtained in the item (1) were plated. Thereafter, 800 μl of the culture medium for ES cells (Table 3) was added to each well.

Subsequently, the ICM obtained in the item (2) was transferred to each of the wells at one cell per well using a micropipette and cultured at 37° C., 5% $CO_2$ for 7 days. The state of implantation was observed every day under a microscope without exchanging the medium with a fresh supply for 3 days of cultivation in order to avoid preventing ICM implantation.

On day 7 of cultivation, the ICM cells were macerated. After removing the culture medium for ES cells from the wells, the dish was once washed with PBS. Three-hundred microliters of 0.25% trypsin/0.02% EDTA was added to each well and immediately removed. Subsequently, the 24-well culture dish was incubated at 37° C. for 1 minute. After confirming cell maceration under a microscope, 500 μl of the ES cell medium was added to each well and thoroughly pipetted using PIPETMAN.

All the above cells were transferred to the wells of a 24-well culture dish previously plated with the feeder cells. After adding 300 μl of the ES cell medium to obtain a total medium volume of 800 μl, the medium was thoroughly mixed to avoid uneven cell plating. The ES cell medium was exchanged with a fresh supply every two days. Since a group of cells deemed ES cells proliferate to colonize within 7 days after cell maceration, the medium was examined every day.

After a colony of ES cells appeared, the cells on the 24-well culture dish were trypsinized and subcultured repeatedly. During this operation, the ES cell medium was replaced with a fresh supply every day or every two days. As a result, more than one ES cell line was obtained from cynomolgus monkey blastocysts.

Example 3

Evaluation of Monkey ES Cells (1) Cynomolgus Monkey ES Cells

Karyotype:

Whether or not the chromosome number was normal (same as the chromosome number of the origin monkey: 2n=42) was determined. As a result, the established ES cell lines were found to retain the normal karyotype.

Pluripotency:

$1 \times 10^6$ cynomolgus monkey ES cells were subcutaneously injected to the inguinal region of an 8-week-old SCID mouse. Five to twelve weeks after injection, tumor formation was observed. After fixation in Bouin's fluid or a para-formaldehyde solution, the tumor was sectioned, subjected to hematoxylin-eosin staining (HE staining) or immunological staining, and examined histologically. In the immunostaining, an antibody against human neuron-specific enolase (NSE), an antibody against glia fibrous acidic protein (GFAP), an antibody against S-100 protein and an antibody against desmin were used since the availability of monkey tissue-specific antibodies was limited.

As a result, the tumor formed was identified as a teratoma consisting of a group of cells derived from ectoderm (neuron and glia), mesoderm (muscle, cartilage, and bone) and endoderm (ciliated epithelium and intestinal epithelium). In the immunohistologic examination, neuron was detected by the antibody against NSE, glia being detected by the antibodies against NSE and GFAP, peripheral nerves being detected by the antibody against NSE, cartilage being detected by the antibody against S-100 protein, and muscles being detected by the antibody against desmin. These results showed that cynomolgus monkey ES cells have the pluripotency into ectoderm-derived cells, mesoderm-derived cells, endoderm-derived cells, and others, more specifically to neurons, glia, muscles, cartilage, bone, ciliated epithelium, intestinal epithelium, and the like.

Figure 3:
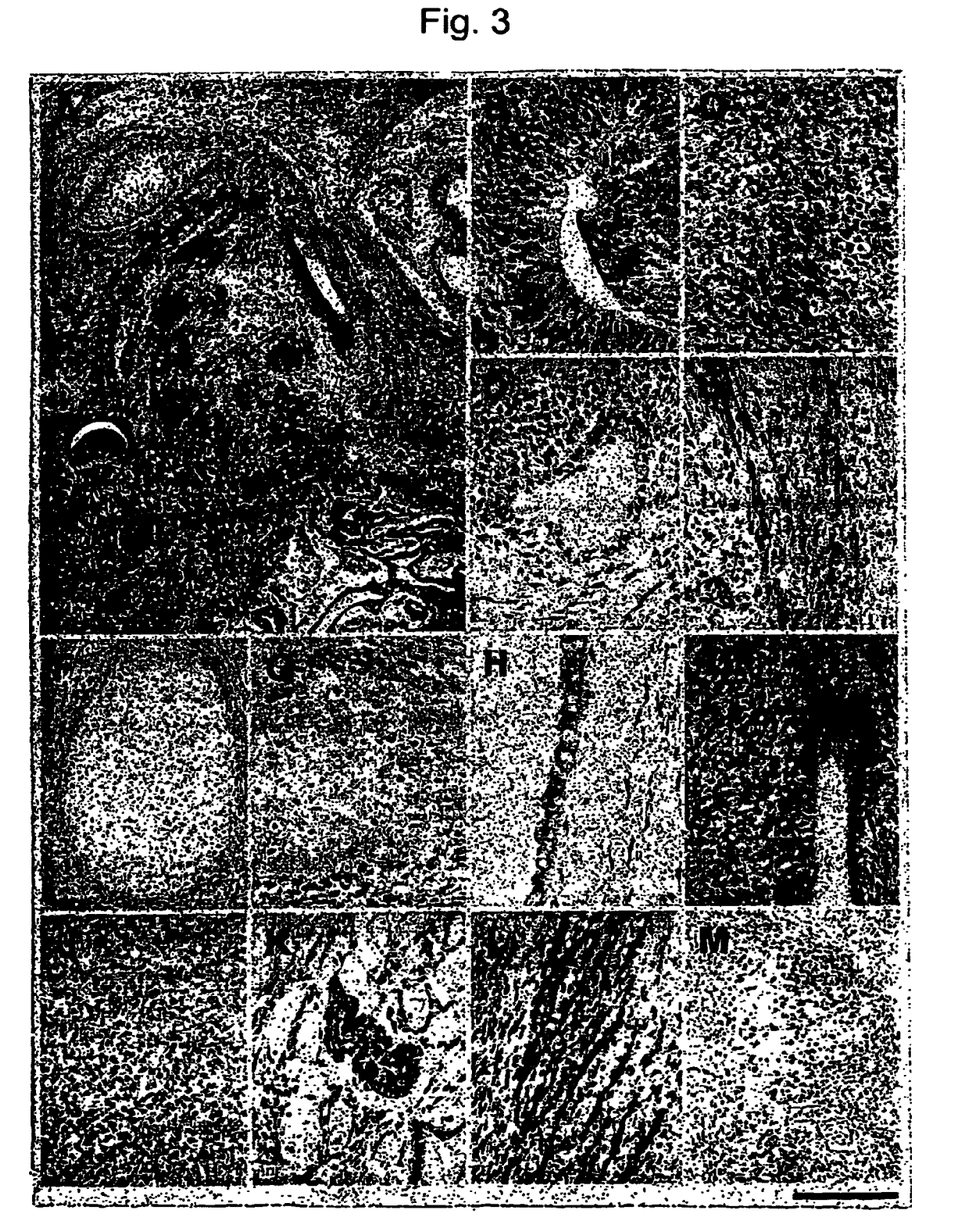

These results of microscopic examination after HE staining are shown in panels A to H of FIG. 3, and those after immunostaining are shown in panels I to M of FIG. 3.

Morphological Features:
1. There were exhibited high nucleus/cytoplasm ratio, conspicuous nucleoli, and colonization.
2. The colonies were more flat, compared to mouse ES cells.

These morphological features are shown in FIG. 1 and panels A and B of FIG. 2.

Expression of Cell Surface Markers:

To confirm the presence or absence of stage-specific embryonic antigens (SSEA), which serve as cell surface markers, immunological staining was carried out by using antibodies against the cell surface markers SSEA-1 (negative control), SSEA-3, and SSEA-4. These antibodies were obtained from The Developmental Studies Hybridoma Bank of the National Institute of Child Health and Human Development. Each cell surface marker for SSEA was 0evaluated by the following procedures: a cell was fixed with 4% para-formaldehyde was reacted with primary antibody. The cell was then reacted with a labeled polymer (Simplestain PO, manufactured by Nichirei Corporation) prepared by coupling peroxidase and a secondary antibody with an amino acid polymer. Thereafter, Simplestain DAB Solution (manufactured by Nichirei Corporation) was added to detect the cell surface markers.

As a result, SSEA-1 was not detected, whereas SSEA-3 and SSEA-4 were detected.

The results of detection of SSEA-4 by the immunostaining are shown in panel D of FIG. 2.

Alkaline Phosphatase Activity:

The alkaline phosphatase activity was determined using HNPP (manufactured by Roche) with Fast-Red TR SaH as the substrate. As a result, the alkaline phosphatase activity was detected. These results of detection are shown in panel C of FIG. 2.

INDUSTRIAL APPLICABILITY

The monkey-derived embryonic stem cell of the present invention is useful for embryological studies, studies of diseases, clinical applications, experimental models, and the like on primates, especially on humans and monkeys. In addition, since the monkey-derived embryonic stem cell can be obtained in a high yield by the method for producing the monkey-derived embryonic stem cell, the method is expected to be applied in embryological studies, studies of diseases, clinical applications, experimental models, and the like on primates, especially on humans and monkeys. Furthermore, the method for screening a reagent for specific differentiation to cell or tissue can be utilized in the screening of a reagent for specific differentiation to cell or tissue which is useful for obtaining the desired differentiated cell or the desired differentiated tissue.

The invention claimed is:

1. A method for producing a *Macaca fascicularis* embryonic stem cell, comprising:
   (a) carrying out fertilization by in vitro fertilization or intracytoplasmic sperm injection using a monkey ovum and a monkey sperm, thereby giving a fertilized ovum;
   (b) allowing the fertilized ovum obtained in the step (a) to differentiate into a blastocyst by in vitro culture at 38° C., under conditions of at 5% $CO_2$, 5% $O_2$ and 90% $N_2$; and
   (c) establishing an embryonic stem cell line using the blastocyst obtained in step (b).

2. A method for producing a *Macaca fuscata* embryonic stem cell comprising:
   (a) carrying out fertilization by in vitro fertilization or intracytoplasmic sperm injection using a monkey ovum and a monkey sperm, thereby giving a fertilized ovum;
   (b) allowing the fertilized ovum obtained in step (a) to differentiate into a blastocyst by in vitro culture at 38° C., under conditions at 5% $CO_2$, 5% $O_2$ and 90% $N_2$; and
   (c) establishing an embryonic stem cell line using the blastocyst obtained in step (b).

3. The method according to any one of claims 1 to 2, wherein a culture medium selected from the group consisting of TALP solution, TALP-HEPES solution and BWW solution is used in step (a).

4. The method according to any one of claims 1 to 2, wherein the in vitro culture in step (b) is a micro-hanging drop culture.

5. The method according to any of claims 1 to 2, wherein the in vitro culture comprising said blastocyst is performed using CMRL-1066.

* * * * *